(12) United States Patent
Frey et al.

(10) Patent No.: US 7,497,870 B2
(45) Date of Patent: Mar. 3, 2009

(54) SYSTEM FOR PROVIDING OPTIMAL INFLATION TO MULTIPLE TEMPERATURE REGULATED BLANKETS AND METHOD THEREFOR

(75) Inventors: William E. Frey, Kingston, MA (US); Joseph Pierre, Brockton, MA (US)

(73) Assignee: Smiths Medical ASD, Inc., Rockland, MA (US)

( * ) Notice: Subject to any disclaimer, the term of this patent is extended or adjusted under 35 U.S.C. 154(b) by 660 days.

(21) Appl. No.: 11/061,871

(22) Filed: Feb. 18, 2005

(65) Prior Publication Data
US 2006/0190064 A1 Aug. 24, 2006

(51) Int. Cl.
*A61F 7/00* (2006.01)

(52) U.S. Cl. .................... 607/107; 607/104

(58) Field of Classification Search .......... 607/96, 607/104–112
See application file for complete search history.

(56) References Cited

U.S. PATENT DOCUMENTS 5,300,098 A 4/1994 Philipot
6,126,681 A * 10/2000 Van Duren et al. ............ 607/96
6,259,074 B1 7/2001 Brunner et al.
6,447,538 B1 * 9/2002 Van Duren et al. ............ 607/96

OTHER PUBLICATIONS

Brochure—Level 1, Inc. "The Equator System." Controlled Convective Warming in a Compact Design, Jan. 2003.

* cited by examiner

*Primary Examiner*—Roy D Gibson
(74) *Attorney, Agent, or Firm*—Louis Woo

(57) ABSTRACT

A convective warmer to which blankets of different dimensions may be connected is capable of providing air to the various blankets at flow rates that optimally inflate those blankets to achieve the optimal clinical result for the patients covered by those blankets. The blanket connected to the warmer may range from a full size adult warming blanket to a pediatric warming blanket. The convection warmer may have multiple fixed air flow rates each selectable by a user, via switch(es) either electronically or mechanically. For the electronic selection of a given flow rate, a motor adaptable to rotate a different speeds is used. To vary the flow rate mechanically, a valve is controlled to vary the amount of air that may pass to the blanket. Instead of different fixed flow rates, variable air flow rates, selectable by the user, may be used. Also, a feedback circuit that maintains the pressure sensed at the outlet of the warmer to a preset pressure may be used to eliminate the need for user intervention.

12 Claims, 17 Drawing Sheets

ONE BUTTON - THREE SPEED
ELECTRONIC FLOW CONTROL

ONE BUTTON - THREE SPEED MECHANICAL FLOW CONTROL

TWO BUTTON - TWO SPEED
ELECTRONIC FLOW CONTROL

TWO BUTTON - TWO SPEED
MECHANICAL FLOW CONTROL

THREE BUTTON - THREE SPEED
ELECTRONIC FLOW CONTROL

THREE BUTTON - THREE SPEED MECHANICAL FLOW CONTROL

VARIABLE SPEED
ELECTRONIC FLOW CONTROL

MANUALLY VARIABLE
ELECTRONIC FLOW CONTROL

MANUALLY VARIABLE
MECHANICAL FLOW CONTROL

REMOTE SENSOR PRESSURE SERVO VARIABLE SPEED ELECTRONIC FLOW CONTROL

REMOTE SENSE PRESSURE SERVO VARIABLE SPEED ELECTRONIC FLOW CONTROL

REMOTE SENSE PRESSURE SERVO VARIABLE SPEED MECHANICAL FLOW CONTROL

SYSTEM FOR PROVIDING OPTIMAL INFLATION TO MULTIPLE TEMPERATURE REGULATED BLANKETS AND METHOD THEREFOR

FIELD OF THE INVENTION

The present invention relates to warming blankets and particularly to a system adapted to optimally inflate each of a plurality of warming blankets irrespective of the different dimensions of those blankets.

BACKGROUND OF THE INVENTION

To hypothermically warm a patient, a convective warmer to which a warming blanket is connected is used. There are various convective warming blanket types that exist in the market today. The various blankets have different dimensions. Prior to the instant invention, a convective warmer, such as the current Level 1 Equator™ warmer, operates at only one speed, so that the same amount of air is output from the warmer irrespective of the size of the blanket connected to the warmer.

Insofar as the different blankets have different sizes, as for example from a full adult size blanket to a neonate blanket, and those blankets have different exhaust capabilities, the existing convective warmers such as for example the aforenoted current Level 1 Equator™ system use different sized outlet hoses adapted to mate with the differently sized blankets. For example, for a regular adult size blanket, a regular outlet hose is used. However, if the convective warmer were to be used to provide heated air to a pediatric warming blanket, which has a smaller dimension than a regular adult blanket, a special hose has to be fitted to the convective warmer so that a portion of the heated air is either blocked or bypassed from the blanket. This is due to the fact that a full size adult blanket requires a higher air flow and thus more volume of air in order to be inflated with the proper pressure, with the heated air coming out of the various holes or slits from the blanket to warm the patient. On the other hand, for a smaller warming blanket such as for example a pediatric blanket, the same amount of air flow into the blanket, if possible, will over inflate the blanket. As a result, to inflate the pediatric blanket, a different hose has to be configured for the outlet of the convective warmer to bypass a portion of the output air so that the pediatric blanket could be properly inflated, and the proper output of heated air provided to warm the child patient covered by the blanket.

There is therefore a need for a convective warmer that is capable of inflating blankets of various dimensions optimally without having to have the outlet hose manually reconfigured for different warming blankets.

SUMMARY OF THE PRESENT INVENTION

The convective warmer of the instant invention is adapted to provide a fluid, such as for example air, at various flow rates, so that the differently dimensioned blankets may each be inflated optimally at a desired pressure.

A first embodiment of the instant invention provides a convective warmer that has a plurality of flow rates selectable by a user. This multiple fixed airflow selection embodiment may incorporate a fluid mover such as for example an air blower that has a predetermined number of speeds, each when selected outputs the fluid at a given flow rate. This multiple fixed flow rate warmer, instead of having its fluid mover or blower operable at multiple fixed speeds, may have a motor that operates at only one speed, but with a controllable valve or restrictor that can be actuated to control the amount of air passing therethrough to control the flow rate of air input to the different blankets.

A second embodiment of the instant invention convective warmer is a variable airflow warmer or system in which the air blower is adapted to operate at variable speeds. By actuating the appropriate switch(es), the user can either increase or decrease the speed of the motor of the blower to thereby variably control the flow rate of the air or fluid provided to the blanket. For this embodiment, a motor of a given fixed speed may also be used, provided that an electro-mechanical valve or restrictor that can be controlled variably is used to control incrementally the flow rate of air provided to the different blankets. With the electro-mechanical valve or restrictor, a user can also control the variable restrictor or valve to either increase or decrease the flow rate of air being provided to a blanket connected to the warmer.

Yet another embodiment of the instant invention is a warmer that can automatically determine the flow rate of air input to the blanket connected to the warmer. For this embodiment, a sensor may be positioned at the outlet hose of the warmer to which the blanket is coupled. By using a feedback circuit, the sensed pressure is maintained at a preset pressure deemed to be appropriate for the blanket that is connected to the warmer. The sensor may also be positioned away from the outlet hose, for example in the cabinet of the warmer, but continue to detect the pressure at the outlet hose, for example by means of a conduit, so that the air pressure at the outlet hose could nonetheless be continuously monitored. The air blower for this embodiment may also be a variable speed blower. Alternatively, a restrictor or valve that could be controlled incrementally to variably control the flow rate of air, in response to the feedback control, may also be used.

The present invention includes therefore a system for providing a fluid to a patient warming blanket that includes a fluid mover for directing the fluid to the outlet of the system, with the outlet establishing a fluid path to the blanket. The fluid warmer is adapted to move the fluid at a plurality of different flow rates. The system further includes a controller for controlling the fluid mover to move the fluid to the blanket, and at least one switch that is actuable by a user to cause the fluid mover to provide the fluid for input to the blanket at a selected one of a plurality of flow rates deemed optimal for the blanket.

The system of the instant invention is further adapted to provide a fluid to patient warming blankets of different dimensions. To achieve this, the system comprises a fluid mover for providing the fluid to a blanket of a given dimension, a controller adapted to variably control the flow rate of fluid to be provided by the fluid mover to the blanket, and at least one switch electrically connected to the controller and actuable by the user to selectively vary the flow rate of the fluid so that the fluid is provided to the blanket of the given dimension at an optimal flow rate. The fluid mover may be an air blower that is adapted to move at various predetermined speeds, or at variable speeds. Alternatively, the fluid or air flow may move at a preset speed, with a restrictor or valve controllably actuated to control the movement of the air at different preset flow rates, or at variable flow rates.

The system of the instant invention also comprises an outlet for establishing a fluid path to the blanket, a fluid mover for directing the fluid to the outlet, a controller for controlling the flow rate of the fluid to the outlet, at least one sensor located relative to the outlet adapted to sense the pressure of the fluid at the outlet, and a circuit for utilizing the sensed pressure of the fluid from the sensor to instruct the controller to, if needed, vary the flow rate of the fluid to the outlet for maintaining the sensed pressure substantially at a preset pressure so that the blanket is properly inflated with the fluid to effect an optimal clinical temperature environment for a patient using the blanket. The sensor may be located at the outlet or at a location away from the outlet.

BRIEF DESCRIPTION OF THE FIGURES

The instant invention will be best understood with reference to the following drawings wherein.

DETAILED DESCRIPTION OF THE INVENTION

Figure 1:
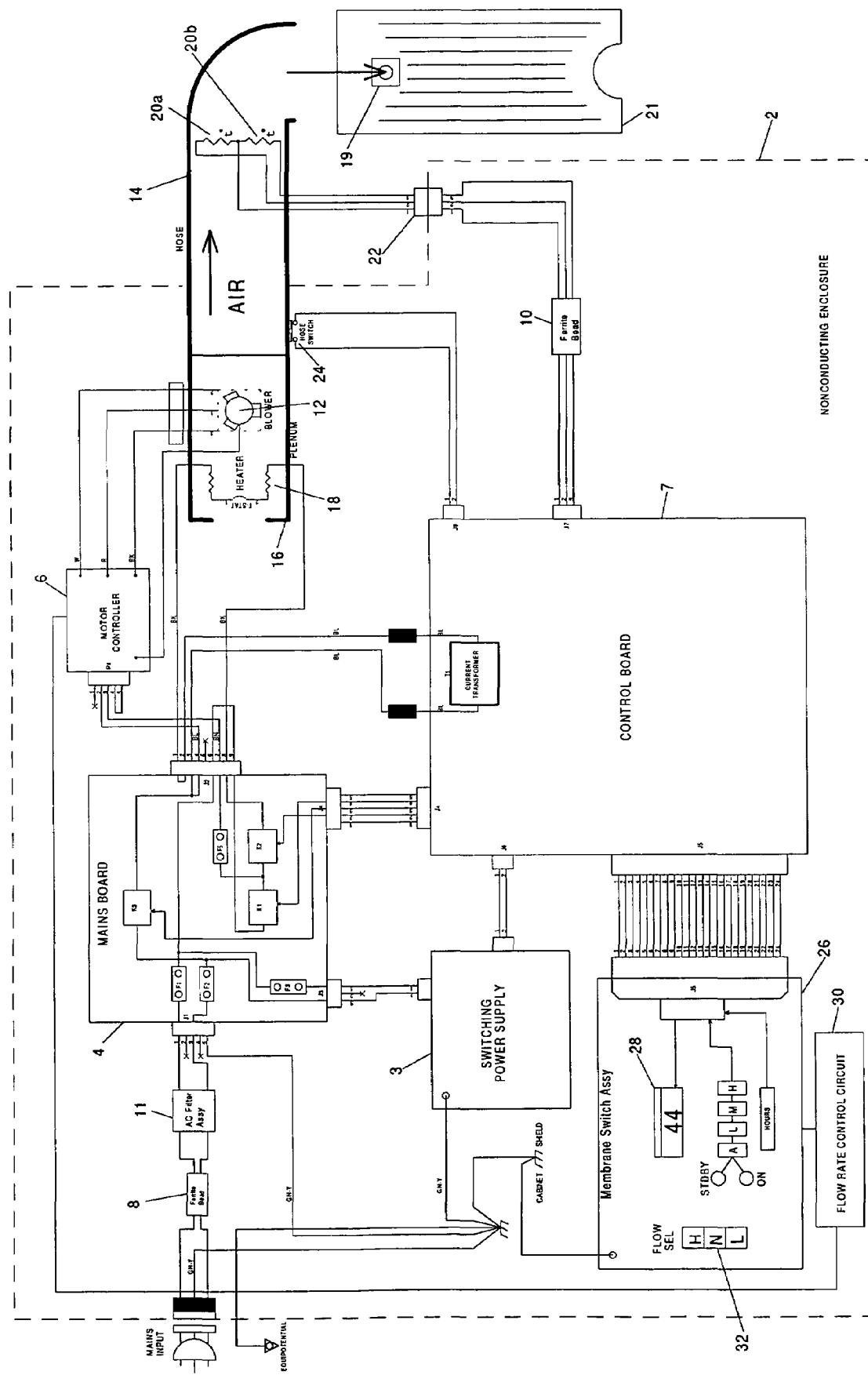
FIG. 1 is a schematic diagram of the overall system of the convection warmer of the instant invention.

A convective warmer of the instant invention is illustrated in FIG. 1. This convection warmer is based on the EQ-5000 model being marketed by the assignee of the instant invention. For the EQ-5000 model, the fluid mover, or the air blower therein, moves or directs the fluid, in this instance air, at one given flow rate irrespective the dimension of the blanket attached to the machine. As a consequence, if the machine was calibrated for inflating an adult size blanket at a given flow rate, and the machine were to be used with a pediatric blanket, the blower would supply air to the pediatric blanket at a flow rate that is much greater than that required by the pediatric blanket, which is of a smaller dimension than that of the adult warming blanket. Prior to the instant invention, to remedy this problem, a special hose is used to bypass the excess air in order to allow the heated air to be input to the pediatric blanket at a flow rate that the pediatric blanket requires.

The warmer system of the instant invention does not require the replacement of the outlet hose for blankets of different dimensions.

With reference to FIG. 1, the convection warmer of the instant invention, shown enclosed by the enclosure designated by dotted line 2, includes a switching power supply 3 and a mains board 4. The AC line portion of the system resides in those circuits, as mains board 4 includes fuses (f) and relays (k) that are used to supply power to both a motor controller 6 and a control board 7. To prevent conductive emission, a ferrite bead 8 is provided at the input of the AC power, and another ferrite bead 10 is provided at the output of the control board. An AC filter assembly 11 filters out transients from the AC power line.

Motor controller 6, with power provided from mains board 4, controls the operation of an air blower 12 which, for the purpose of this invention, may be considered a fluid mover that moves, directs or blows a fluid such as air to an outlet hose 14. Blower 12 is shown to be located in a plenum 16, which also has resided therein a heater 18 for heating the air being blown by the blower 12 to hose 14, which is connected to the outlet of the system. In practice, hose 14 may be considered the outlet of the convection warmer to which a warming blanket such as 21 is connected via its inlet opening 19.

Control board 7 contains, among other circuits, a power on and self-test circuit, a temperature control circuit that monitors thermistor 20a at the distal end of the hose 14 to maintain the heated fluid at a given range of temperature for example approximately 36-44° centigrade, an under temperature indicator to indicate that the temperature is below a preset temperature and an overtemp supervisory circuit that monitors thermistor 20b at the distal end of hose 14 for ensuring that the temperature of the heater does not exceed a given temperature. The respective operations of most of these circuits are given in U.S. Pat. No. 6,259,074, the disclosure of which is incorporated by reference herein.

As shown, thermistors 20a and 20b are connected to control board 7 via a removable socket 22. Also connected to control board 7 is a hose switch 24 that indicates whether the air hose 14 is attached to the system. If per chance hose 14 is removed or comes loose, hose switch 24 would detect that no air hose is attached, and the system will provide an alarm or an indication to the user that there is no air hose at, or that the air hose is not secured to the outlet of the system.

Further provided in system 2 is a membrane switch assembly 26, which is the front panel of the system. It includes indicators for indicating whether the system is turned on or at a standby condition. Also provided on the front panel of the FIG. 1 embodiment are four switches, A, L, M and N indicating the ambient, low, medium and high temperatures, respectively, of the temperature of the air being heated by the heater. An indicator 28 is provided on the front panel for indicating the temperature at the distal end of hose 14.

For the instant invention, a flow rate control circuit 30 is in electrical communication with the membrane switch assembly 26. Also provided to membrane switch assembly 26 are buttons or switches that may designate the speed with which the blower operates to move the air to the outlet hose. For the exemplar embodiment shown in FIG. 1, push button switches 32 may be used for designating a low speed (L), a normal speed (N), and a high speed (H) for the air blower. In place of the push button switches, rotary switches and other types of switches may also be used. Further, as to be discussed later, a switch(es) that when continuously pushed will cause the speed of the blower to increase/decrease may also be used.

The flow rate control circuit 30, in addition to being in electrical communication with the membrane switch assembly 26, is also in electrical communication with motor controller 6, which controls the speed with which blower 12 operates per instructed by the user's actuation of the switch (es) on the front panel.

Figure 2:
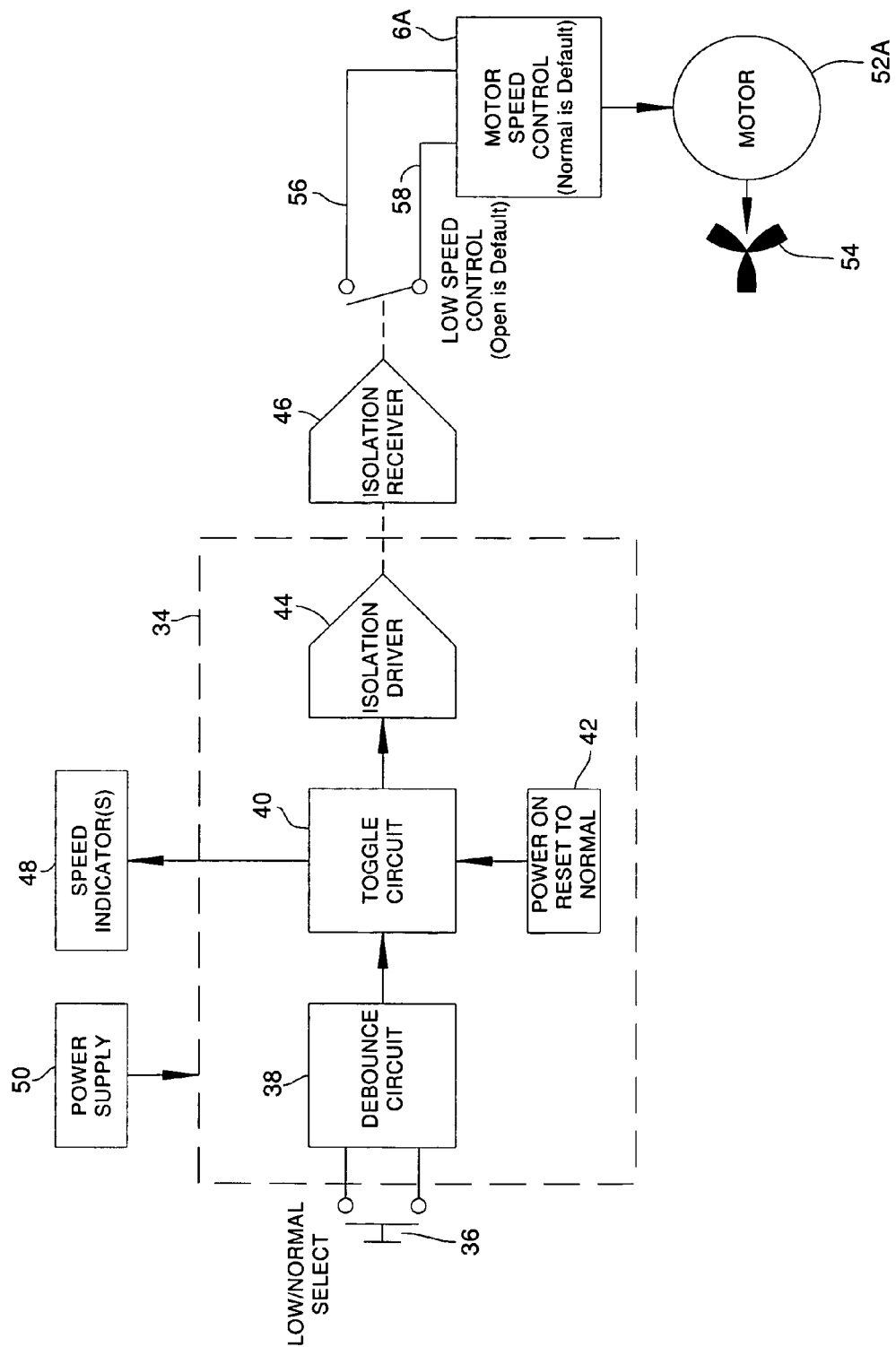
FIG. 2 is a block diagram illustrating a one-button/two-speed electronic flow control adapted to be used with the convective warmer system of FIG. 1.

With reference to FIG. 2, a first embodiment of the flow rate control circuit 30 of FIG. 1 is shown. The FIG. 2 embodiment illustrates a one-button/two-speed electronic flow control circuit that includes a main control circuit 34 designated within the dotted line. For this embodiment, a single switch 36, in the form of a low/normal select switch, is used. Circuit 34 has a debounce circuit 38, electrically activated by switch 36, for ensuring the no bouncing occurs when switch 36 is actuated. The output of the debounce circuit 38 is connected to a toggle circuit 40, which further has connected to it a power on reset to normal circuit 42. Circuit 42 is used to set the circuit to a normal speed condition when the machine is powered on. The output of toggle circuit 40 is provided to an isolation driver 44, which in turn is coupled to an isolation receiver 46. The purpose of toggle circuit 40 is to actuate the circuit in either one or the other condition, in this instance either a normal speed or a low speed. The state in which toggle circuit 40 has been actuated is indicated by speed indicator 48, which may be provided to the front panel or the membrane switch assembly 26 of the machine. Power supply 50 provides the power to the circuit of FIG. 2.

When actuated by switch 36, the state in which the blower is to be driven is provided to isolation receiver 46, which purpose along with isolation driver 44 is to isolate circuit 34 from the motor speed control 6A, if necessary, which may be considered for this discussion to be the same as motor controller 6 shown in the overall system diagram of FIG. 1. For the FIG. 2 embodiment, by default, speed is set to normal, as the low speed control is open by default. Upon actuation, the motor speed control 6A is activated to either the normal speed, or the low speed for driving motor 52, which along with fan 54, form the air blower 12 shown in FIG. 1. For the FIG. 2 illustration, although not shown, it should be appreciated that there is at least one resistor, as well as a potentiometer connected in series at either one of the input lines 56 or 58. The resistance provided by the fixed resistor and the potentiometer is used to adjust the speed with which controller 6a controls motor 52a to rotate at either a normal speed, if a regular warming blanket is used, or a low speed, for inflating a smaller dimensioned warming blanket such as a pediatric blanket.

With the variable resistance provided to lines 56 and 58 for the motor speed controller, the optimum flow rate, in terms of the normal and the low speeds, are configured for inputting the optimal amount of air into the different dimensioned blankets to therefore achieve an optimal clinical result that those blankets may bestow on a patient, without the machine having to have its outlet hose changed when a different dimensioned blanket is used. Thus, for the FIG. 2 embodiment, after power-up, when switch 36 is first pushed, the speed of the blower is switched from normal to low, if a smaller dimensioned blanket were connected to the warmer.

If the blanket coupled to the warmer were to be replaced by an adult blanket, upon further actuation of switch 36, the speed of blower 12 may again be set to a normal speed.

Figure 3:
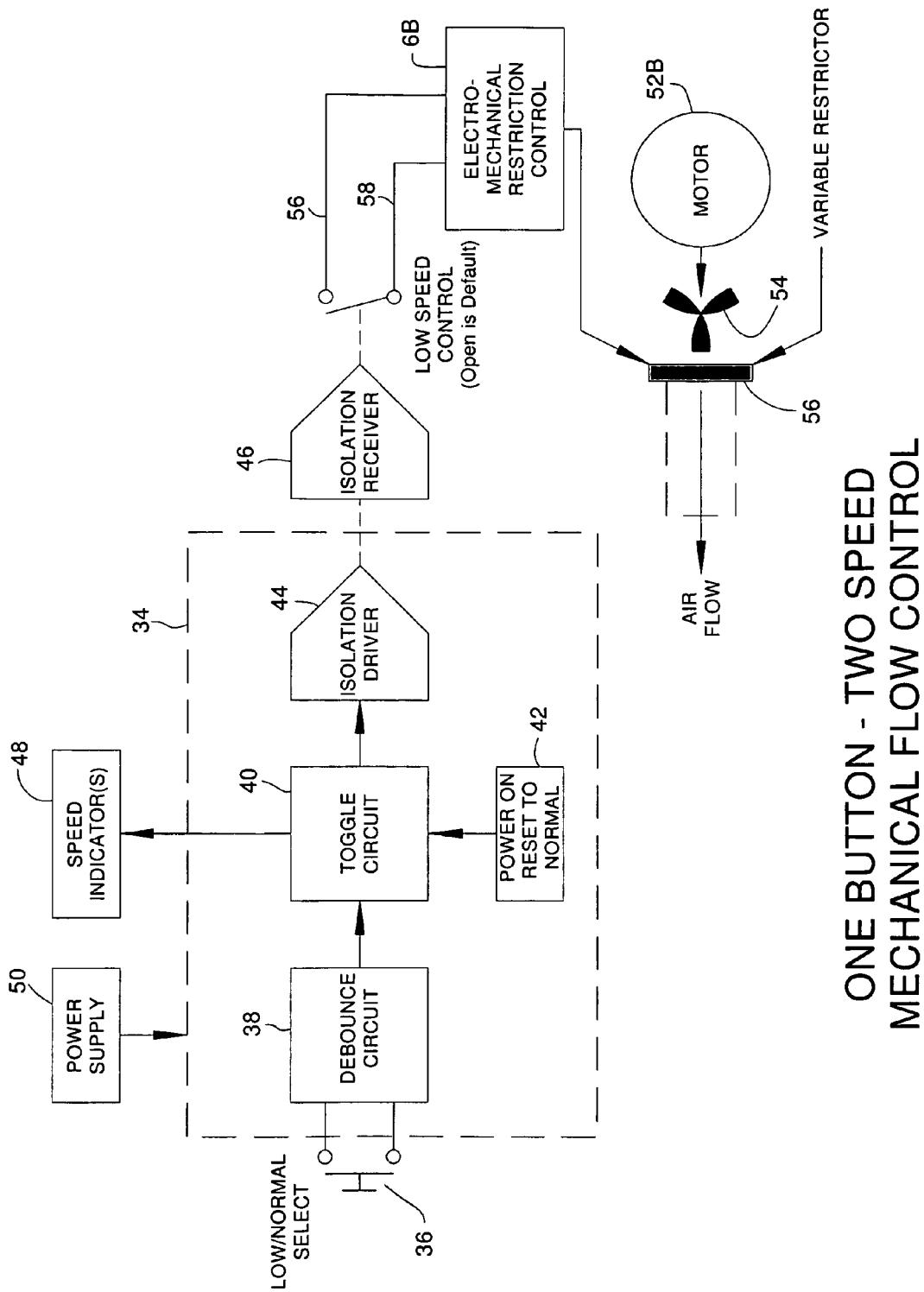
FIG. 3 is schematic diagram of a one-button/two-speed mechanical flow control circuit adapted to be used with a convection warmer such as for example that shown in FIG. 1.

FIG. 3 illustrates also a one-button/two-speed flow rate control circuit. The components in the FIG. 3 embodiments, and the later embodiments to be discussed, that are the same as the components discussed earlier are labeled the same. For the FIG. 3 embodiment, instead of a motor speed controller 6a that is adapted to control motor 52a in either a normal or low speed, the motor controller is replaced by an electro-mechanical restriction controller 6b, which is an electro-mechanical controller that may be in the form of a servomotor, or a solenoid in the case of a dual speed control, that controls a restrictor 56, which may be a valve having an opening that could be variably adjusted to vary the amount of air that may pass through. For the FIG. 3 embodiment, motor 52b may be a fixed speed motor that rotates fan 54 at a single speed, the speed being predetermined to move a sufficient amount of air that could properly inflate the largest available warming blanket when normal speed is selected. When restricted by valve 56 the amount of air is reduced to properly inflate a smaller blanket, for example, a pediatric blanket. For either case, the amount of air output from the convection warmer is adapted to fill at an optimal rate the warming blanket, at a sufficient pressure so that heated air continues to leak out of the strategically placed slits or slots of the blanket for warming the patient covered by the blanket.

Figure 4:
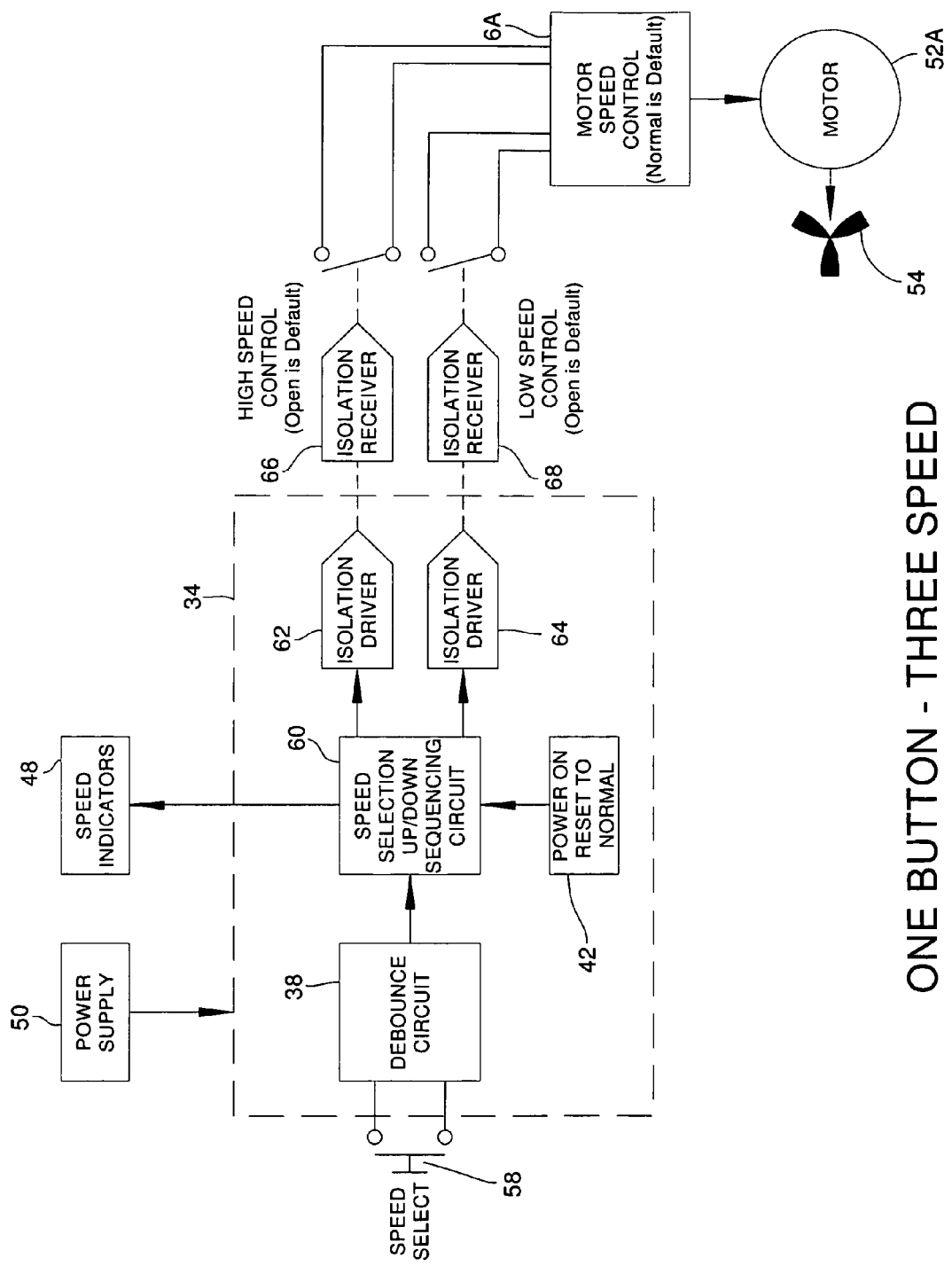
FIG. 4 is a one-button/three-speed electronic flow control circuit adapted to be used with a convection warmer.

FIG. 4 shows a one-button/three-speed electronic flow circuit for effecting three or more air flow rates by means of a single speed select switch. For the FIG. 4 embodiment, a speed selection up/down sequencing circuit 60 is provided in flow control circuit 34. Further, since there is more than one speed, two pairs of isolation driver/isolation receivers are used. Here an isolation driver 62 is coupled to an isolation receiver 66, while an isolation driver 64 is coupled to an isolation receiver 68. For this embodiment, motor 52a is a variable speed motor that is adaptable to rotate in at least three speeds. In operation, when speed select switch 58 is actuated, assuming that the system has been powered on and the default setting was set to normal, the speed of motor 52a may be reduced to a low speed. A second actuation of switch 58 causes sequencing circuit 60 to select the next speed, for example the high speed. Yet another actuation of switch 58 selects the next speed, for example normal, that motor 52a would operate to drive fan 54.

For the FIG. 4 embodiment, assuming that there are three speeds, from empirical studies, it is found that the flow rate for normal speed is approximately 1750 ft/min, the flow rate for high speed is approximately 2100 ft/min and the flow rate for low speed is approximately 1300 ft/min. These flow rates signify the different speeds of air coming out at the end of the connector hose, and are related to respective volumes of air provided to the blankets. The diameter of the hose and the area of the hose through which air passes are taken into consideration. For the various flow rates noted, it is assumed that the high speed flow rate is approximately 25% higher than the normal speed flow rate, and the low speed flow rate is approximately 25% below the normal speed flow rate.

Figure 5:
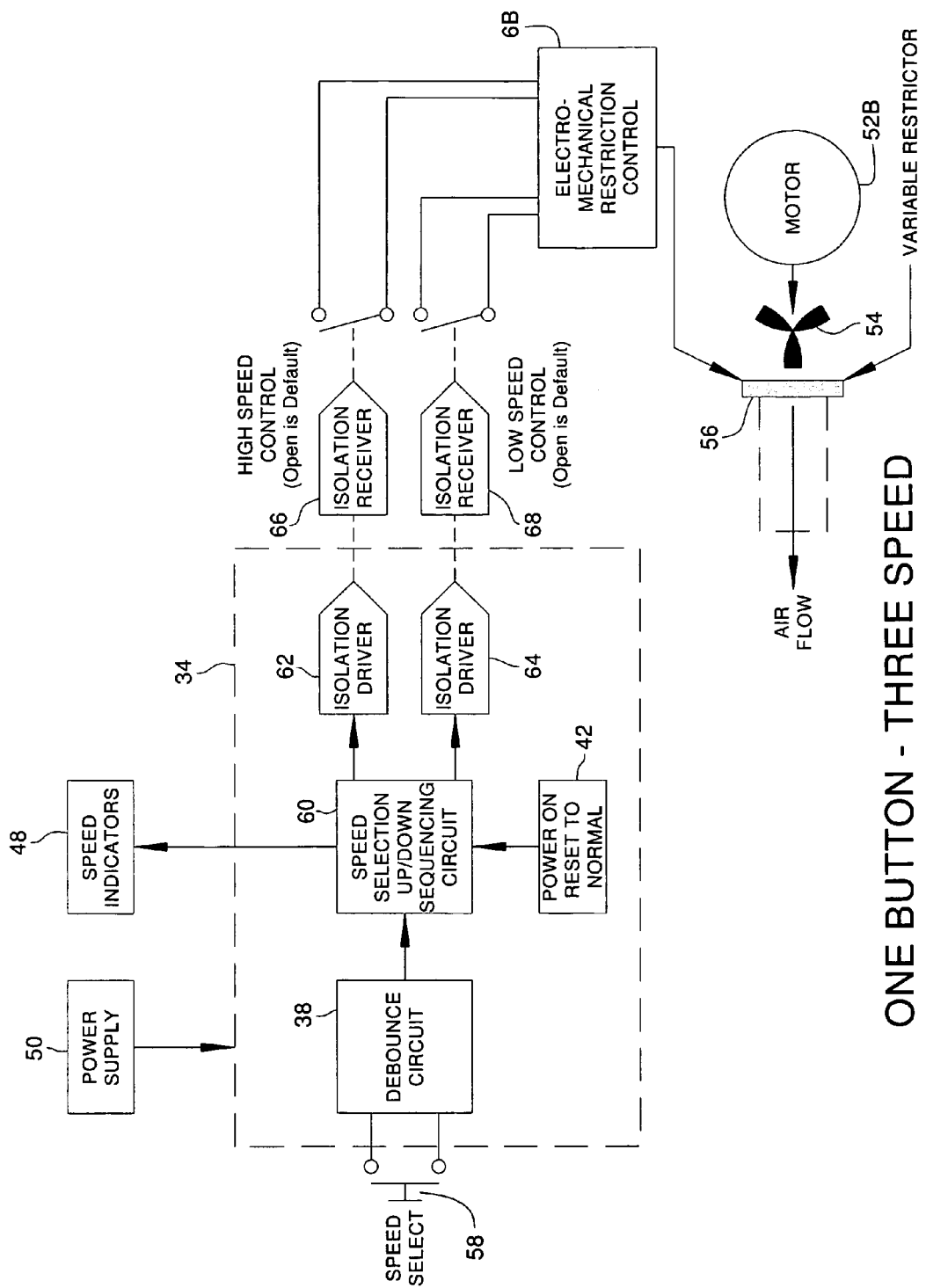
FIG. 5 is a one-button/three-speed mechanical flow control circuit adapted to be used with a convection warmer.

FIG. 5 also illustrates a one-button three-speed flow control circuit that is the same as the embodiment of FIG. 4. However, for this embodiment, the amount of air provided to the blankets is controlled by a valve which opening can be varied to enable different amounts of air to pass through, so that the flow rate of the air provided to the blanket connected to the warmer may be controlled.

For the FIG. 4 and FIG. 5 embodiments, with three speeds, three different types of the blankets with three different dimensions may be used with the same warmer. Even though only three speeds are shown in the FIG. 4 and FIG. 5 embodiments, it should be appreciated that a plurality of speeds, not limited to three, is also envisioned for the instant invention.

Figure 6:
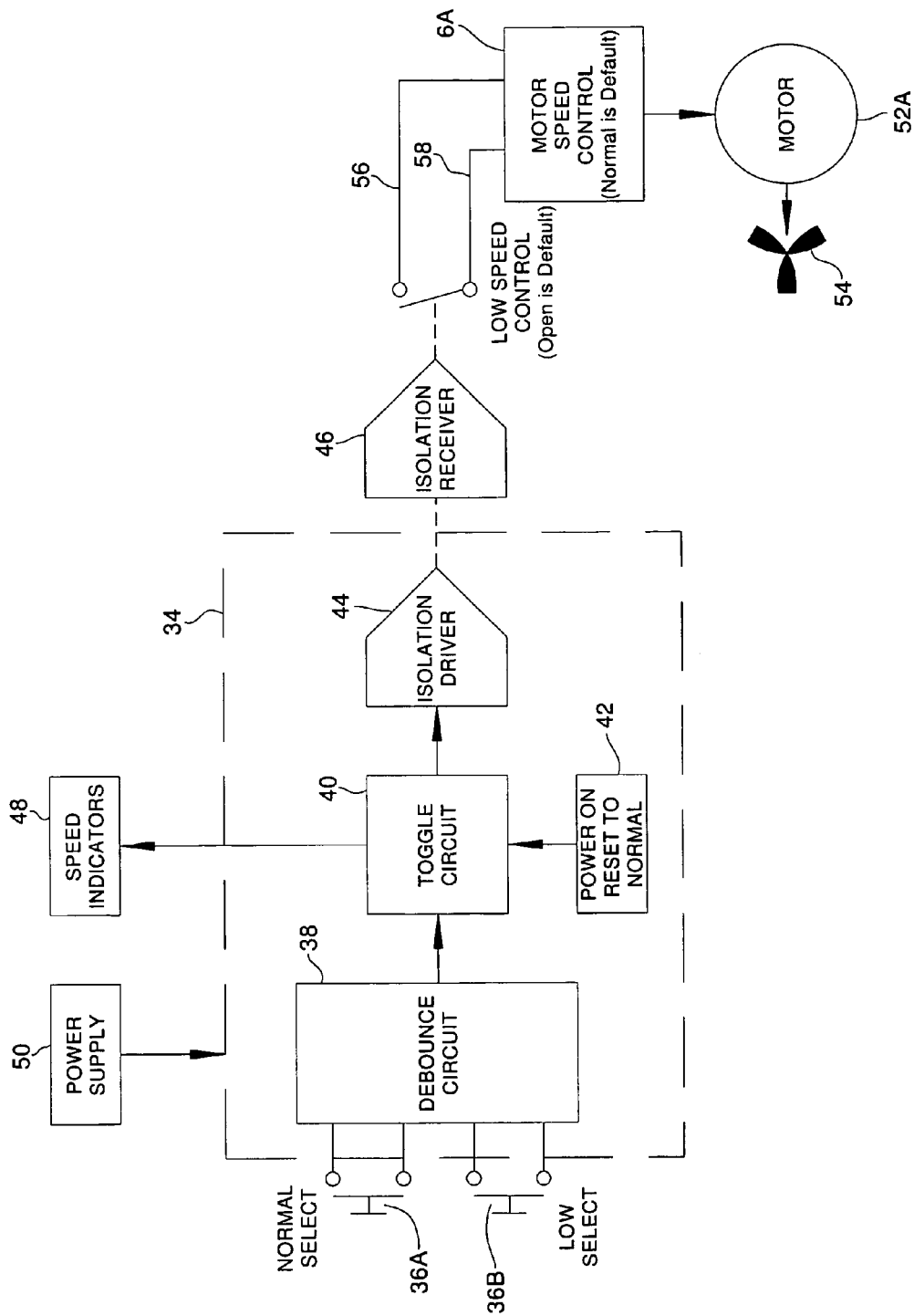
FIG. 6 is a two-button/two-speed electronic flow control circuit adapted to be used with a convection warmer.

FIG. 6 illustrates a two-button/two-speed electronic flow rate control circuit that is similar to the circuit shown in the FIG. 2 embodiment. For the FIG. 6 embodiment, however, there are two switches 36a and 36b which allow a user to actuate either a normal speed or a low speed directly, albeit the normal speed is the default speed.

Figure 7:
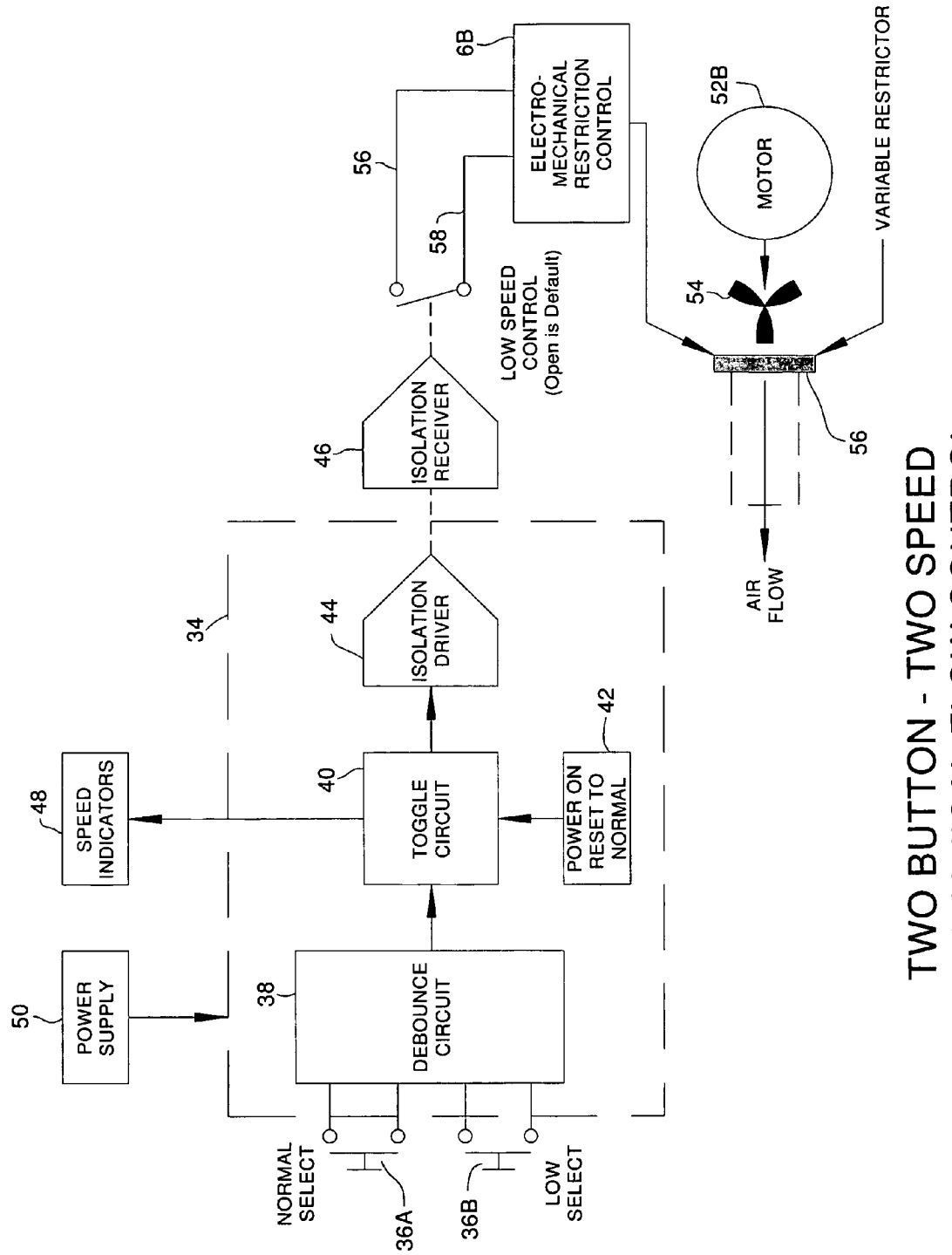
FIG. 7 is a two-button/two-speed mechanical flow control circuit adapted to be used with a convection warmer.

The FIG. 7 embodiment illustrates a two-button/two-speed mechanical flow rate control circuit that is similar to the circuit of the FIG. 3 embodiment, but the two switches 36a and 36b being used to directly actuate valve 56 to allow either a normal flow rate or a low flow rate for air to be moved by the air blower to the outlet of the machine. For both the FIG. 6 and FIG. 7 embodiments, two blankets of different dimensions may each be inflated optimally under the desired pressure.

Figure 8:
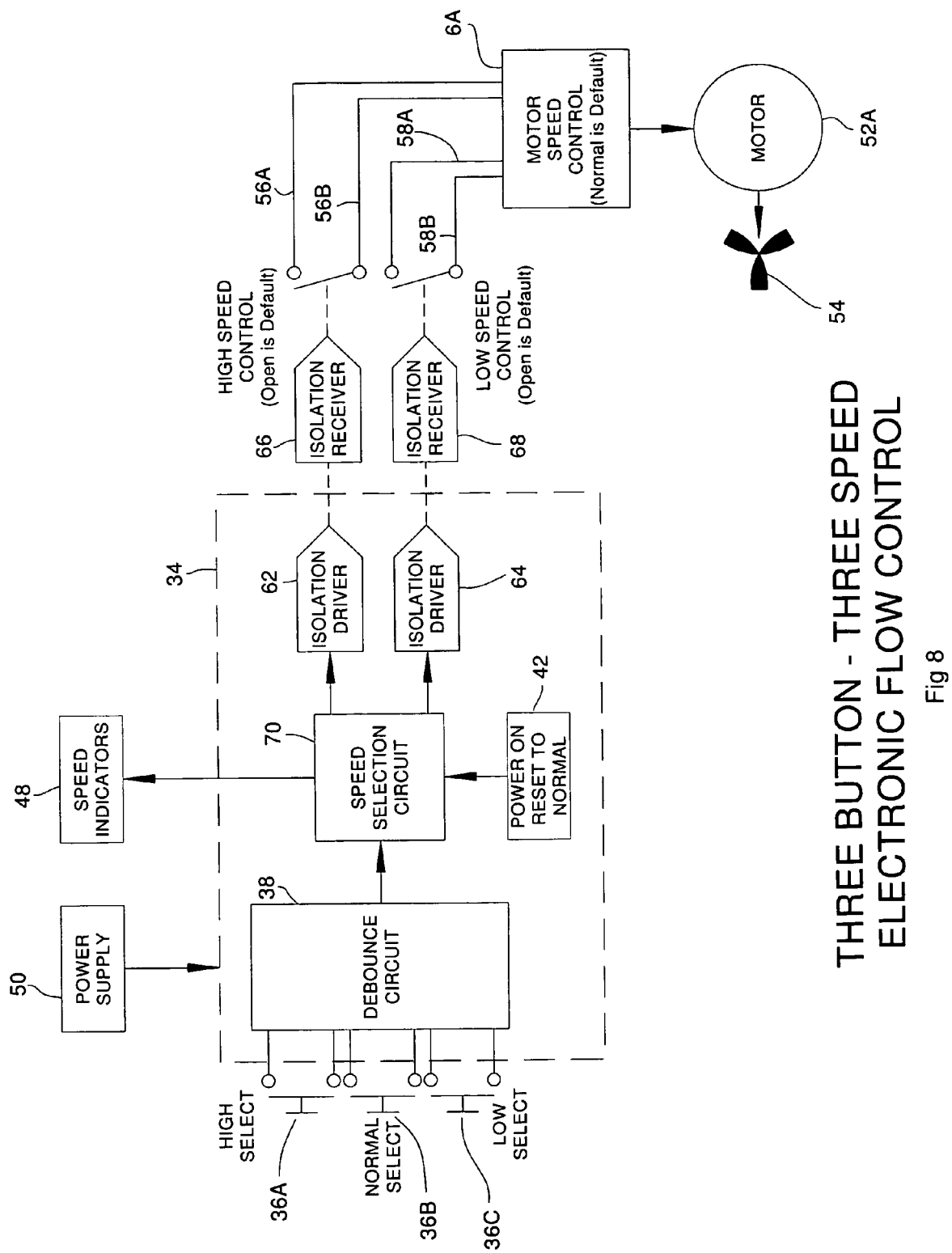
FIG. 8 is a three-button/three-speed electronic flow control block diagram adapted to be used with a convection warmer.

FIG. 8 illustrates a three-button/three speed electronic flow rate control circuit that is similar to the circuit shown in the FIG. 6 embodiment. The difference between the FIG. 8 embodiment and the FIG. 6 embodiment is the additional switch which enables a user to directly actuate a circuit to either a high, normal or low speed for providing air to inflate multiple differently dimensioned blankets. For the FIG. 8 embodiment, motor 52A is configured to operate at three preset speeds—namely high, normal and low speeds for directing the heated air at high, normal and low flow rates, respectively, to the outlet hose.

Figure 9:
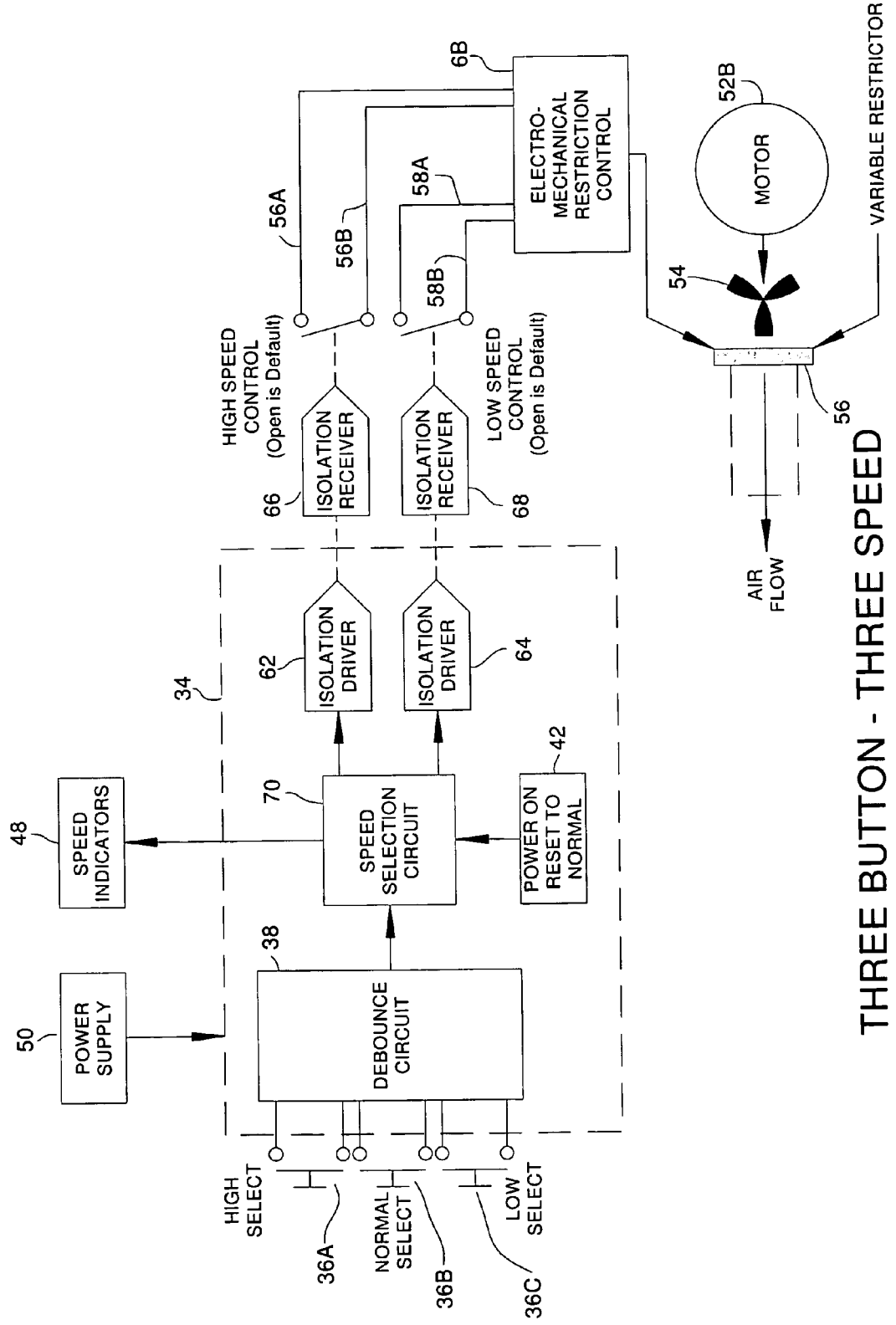
FIG. 9 is a three-button/three-speed mechanical flow control circuit adapted to be used with a convection warmer.

FIG. 9 illustrates a three-button/three speed mechanical flow control circuit that is similar to the FIG. 7 circuit. For the FIG. 9 embodiment, instead of two switches, three switches 36a-36c are used to provide a user the ability to directly select any one of three speeds by using valve 56 to control the flow rate of air provided by the blower to the blanket that is connected to the outlet hose of the system.

Figure 10:
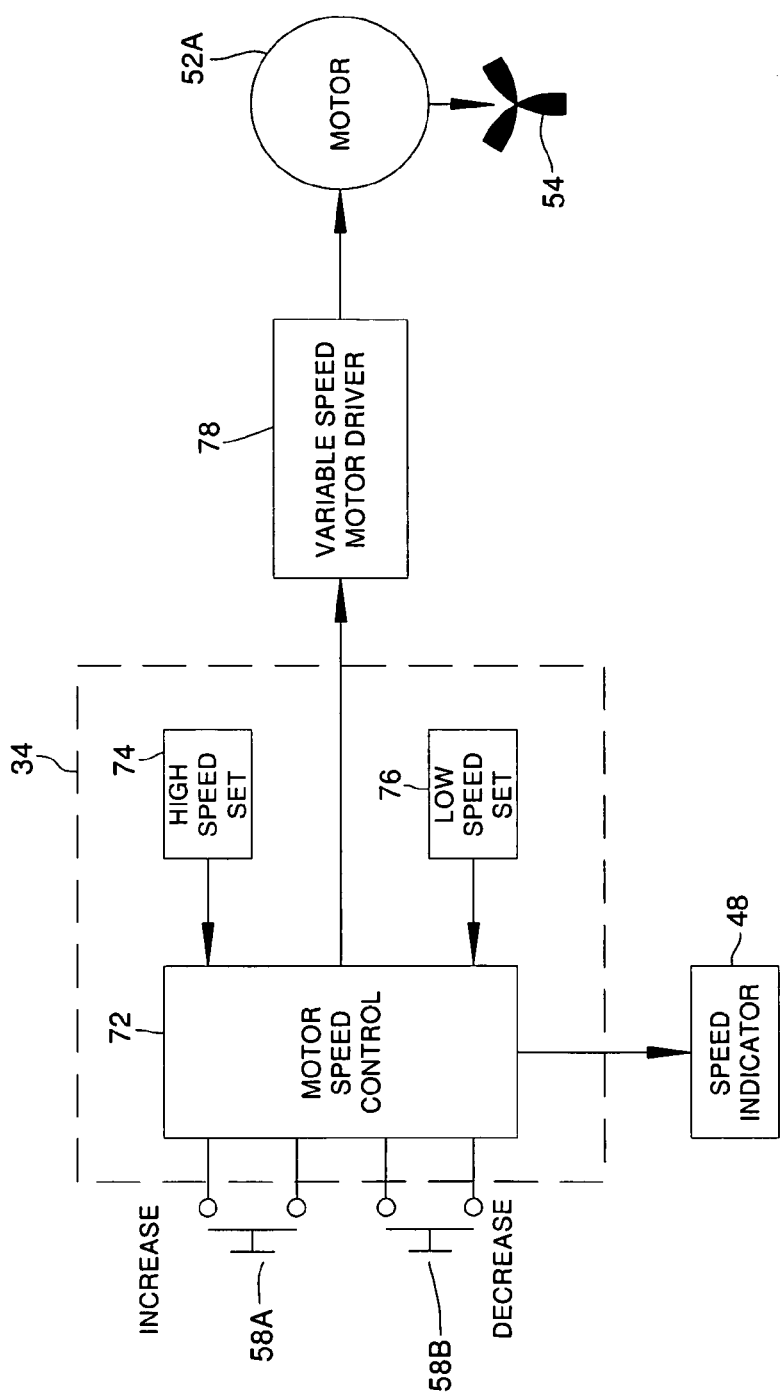
FIG. 10 is a variable air speed electronic flow control circuit adapted to be used with a convection warmer.

FIG. 10 is an illustration of a variable speed electronic flow rate control circuit that comprises two switches 58a and 58b, with one of the switches being used to increase the speed of a variable speed motor while the other being used to decrease the speed of the motor. In the circuit, a motor speed control subcircuit 72 is provided to receive the inputs from switches 58a and 58b. Further provided are a high speed set circuit 74 and a low speed set circuit 76 for setting the high speed limit and the low speed limit, respectively, which motor 52A is adapted to operate for this embodiment. The range defined by the high speed limit and the low speed limit is the range in which the variable speed motor driver 78 controls the speed of motor 52a, which in turn drives fan 54 at the speed selected for moving air to the outlet hose. The speed selected is indicated by speed indicator 48. For the embodiment of FIG. 10, as the air blower could be set to any of the speeds defined between the high and low speed limits, any of a plurality of warming blankets may be connected to the convective warmer so that the blanket that is connected to the warmer, irrespective of its dimension, may be optimally inflated at the desired pressure. The variable speed motor driver 78 of the FIG. 10 embodiment may be a variable frequency motor driver that drives the three phase motor 52A by varying its input DC voltage. One such variable speed motor driver is made by the Fasco Company of Missouri under product No. 8110-9089

Figure 11:
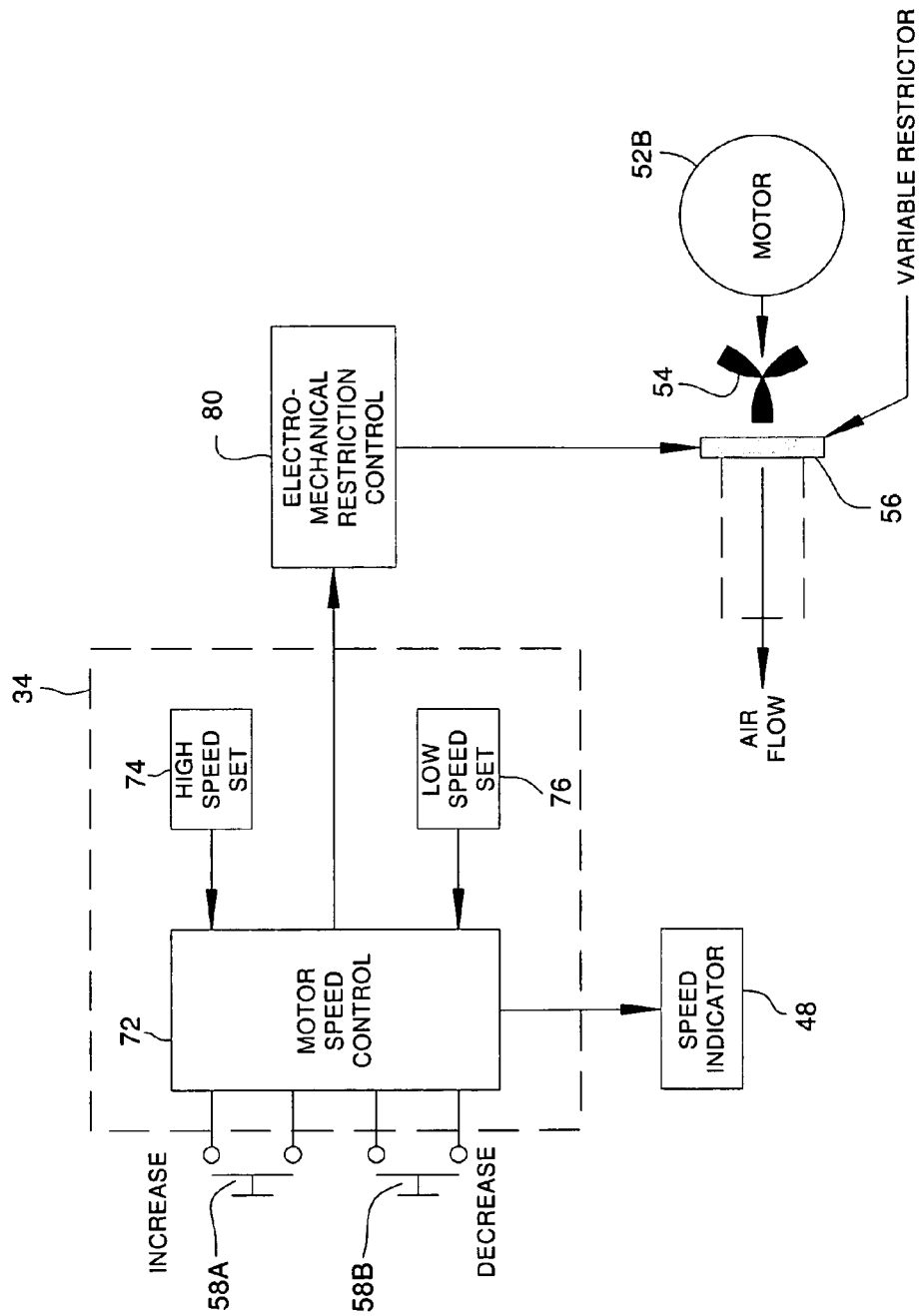
FIG. 11 is a schematic block diagram of a variable air speed mechanical flow control circuit adapted to be used with a convection warmer.

FIG. 11 illustrates a variable speed flow rate control circuit that is a mechanical variation of the FIG. 10 embodiment. Here, the switches 58a and 58b may be actuated by the user to selectively vary the amount of air to be provided to the outlet hose by means of a variable restrictor that may be in the form of a variable valve. The valve is controlled by an electromechanical restriction control circuit 80, driven by the motor speed control circuit 72. As with some of the other embodiments, motor 52b moves air at a fixed rate. The flow rate of air is varied by controlling valve 56.

For both embodiments of FIGS. 10 and 11, the high speed limit may for example be set at 2100 ft/min while the low speed limit may be set for example to 1300 ft/min. The just noted high and low speed limits may of course be varied, depending on potential new types of warming blankets that may come onto the market. Also, the speed indicator 48 for both of the FIGS. 10 and 11 embodiments, insofar as those embodiments relate to variable speed control of the motor or blower, may be a bar graph indicator that provides a relative speed indication or a numerical display indicating relative speed.

Figure 12:
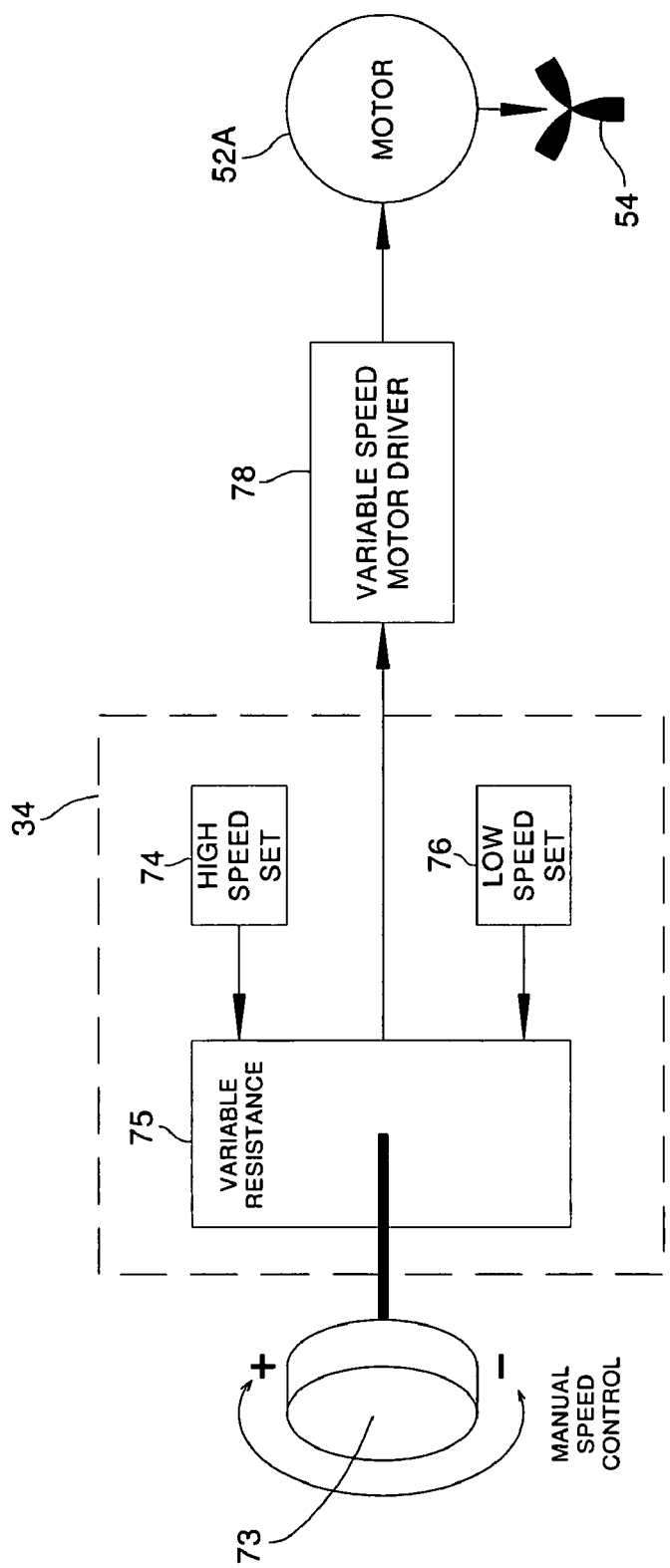
FIG. 12 is a schematic block diagram of a variable air speed electronic speed control actuated by a rotary potentiometer or switch that can variably control the speed of a blower adapted to be used with a convection warmer.

With reference to FIG. 12, the two user actuatable switches 58a and 58b have been replaced by a single knob or control switch 73 that works cooperatively with a variable resistance circuit 75. As shown, depending on which direction knob 73 is rotated, the speed of motor 52a can either be increased or decreased. Other than the number of user actuable switches, the control circuit of FIG. 12 operates in the same fashion as that of FIG. 10. Knob 73 may control a potentiometer and the speed indicator may be represented by the rotational position of the knob.

Figure 13:
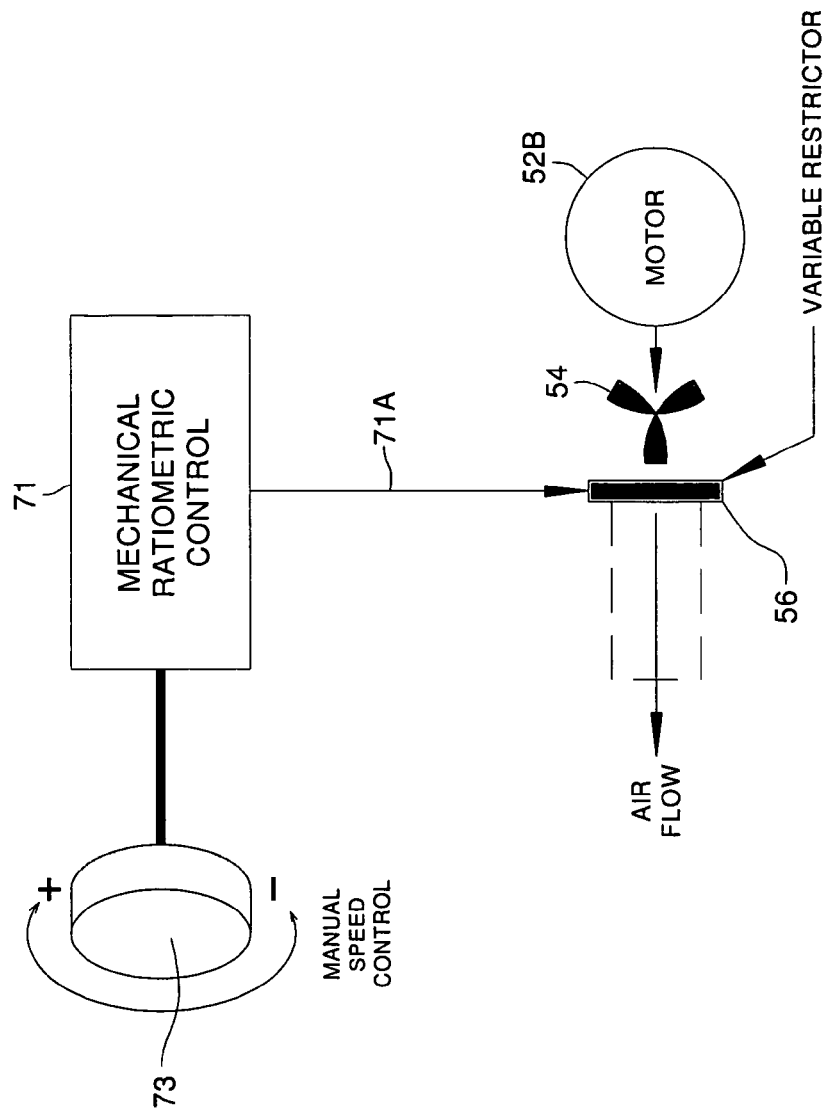
FIG. 13 is a schematic block diagram of a variable restrictor control actuated by a rotary knob that can variably control the air speed of a blower adapted to be used with a convection warmer.

FIG. 13 shows a variable restrictor control, adapted to be used with a convection warmer, that is actuated by rotary knob or control switch 73 that variably controls the amount of air output from a blower. Specifically, knob 73 is coupled to a mechanical ratiometric control 71 that is a mechanism that, in response to the rotation of knob 73, proportionally controls the opening of variable restrictor 56 via gear or lever through 71a to allow a corresponding amount of air to pass therethrough. The FIG. 13 embodiment is therefore a substantially mechanical control that mechanically performs the same function as the previous mentioned embodiments for controlling the amount of air output to a blanket by controlling a variable valve or restrictor.

The embodiments discussed thus far, namely the FIGS. 2-13 embodiments, all relate to flow rate control circuitries that are actuated by a user. The herein discussed embodiments, in contrast, do not require any intervention by the user. In particular, the embodiments disclosed in FIGS. 14-17 illustrate different convective warming system that continuously adjust the flow rate of the air being provided to the blanket connected to the outlet hose of the system by feedback.

Figure 14:
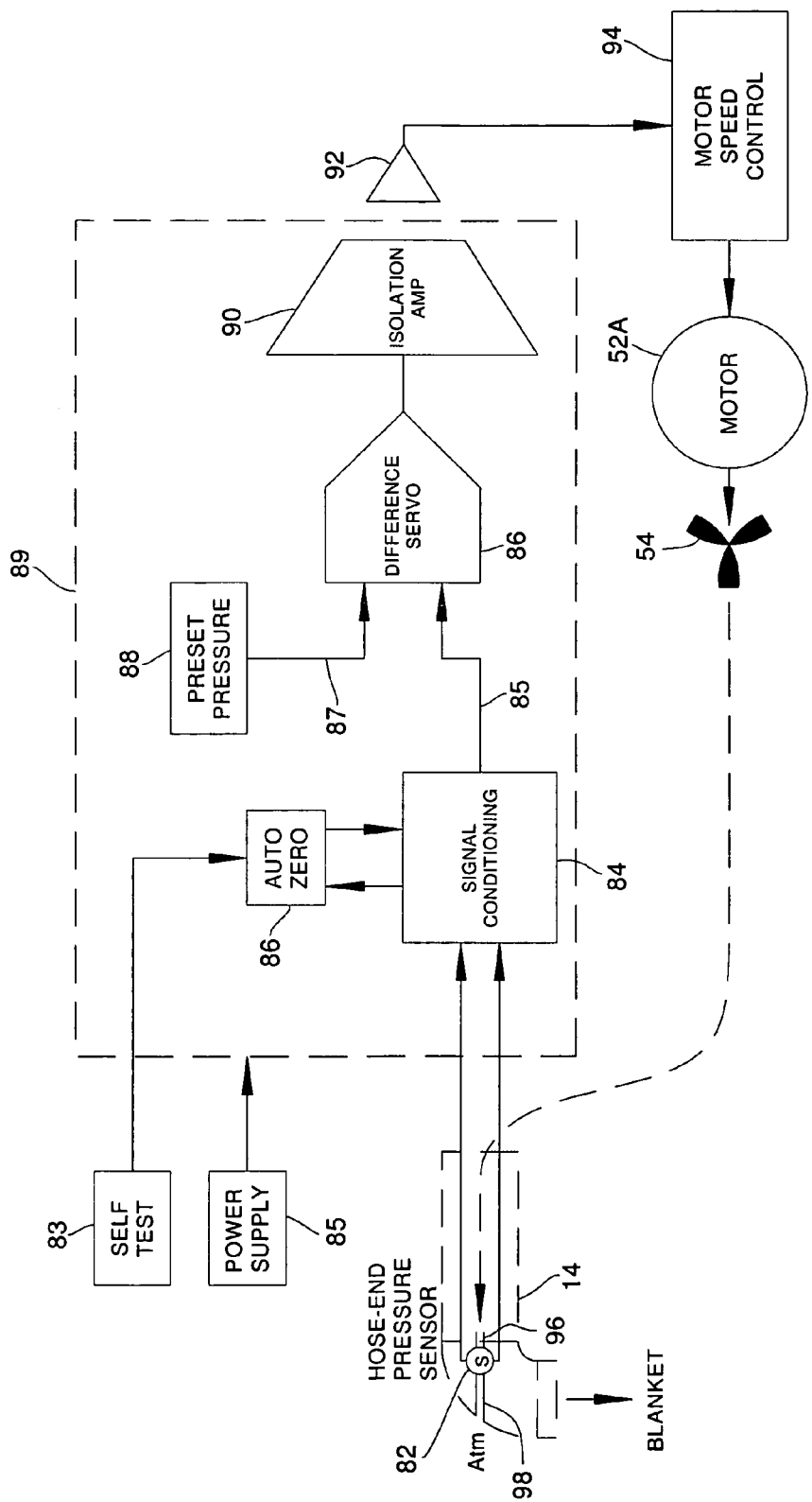
FIG. 14 is a schematic block diagram of a remote sensor pressure servo circuit that can variably control the speed of a blower adapted to be used with a convection warmer.

With reference to FIG. 14, a remote sensor pressure servo variable speed electronic flow rate control circuit is shown. In particular, the FIG. 14 embodiment has a sensor 82 positioned at the end of hose 14, which is used for inserting or mating with the opening or inlet 19 of warming blanket 21 shown in FIG. 1. For the embodiment of FIG. 14, as well as the various embodiments of this invention, hose 14 may also be considered as the outlet of the machine of the instant invention. As shown, sensor 82 detects the pressure of the air, that passes over it, as the air is being provided to the warming blanket. The sensor may be in the form of a diaphragm with a semiconductor, and is made by a number of companies including the Motorola Company under product No. MPX2052D.

Figure 15:
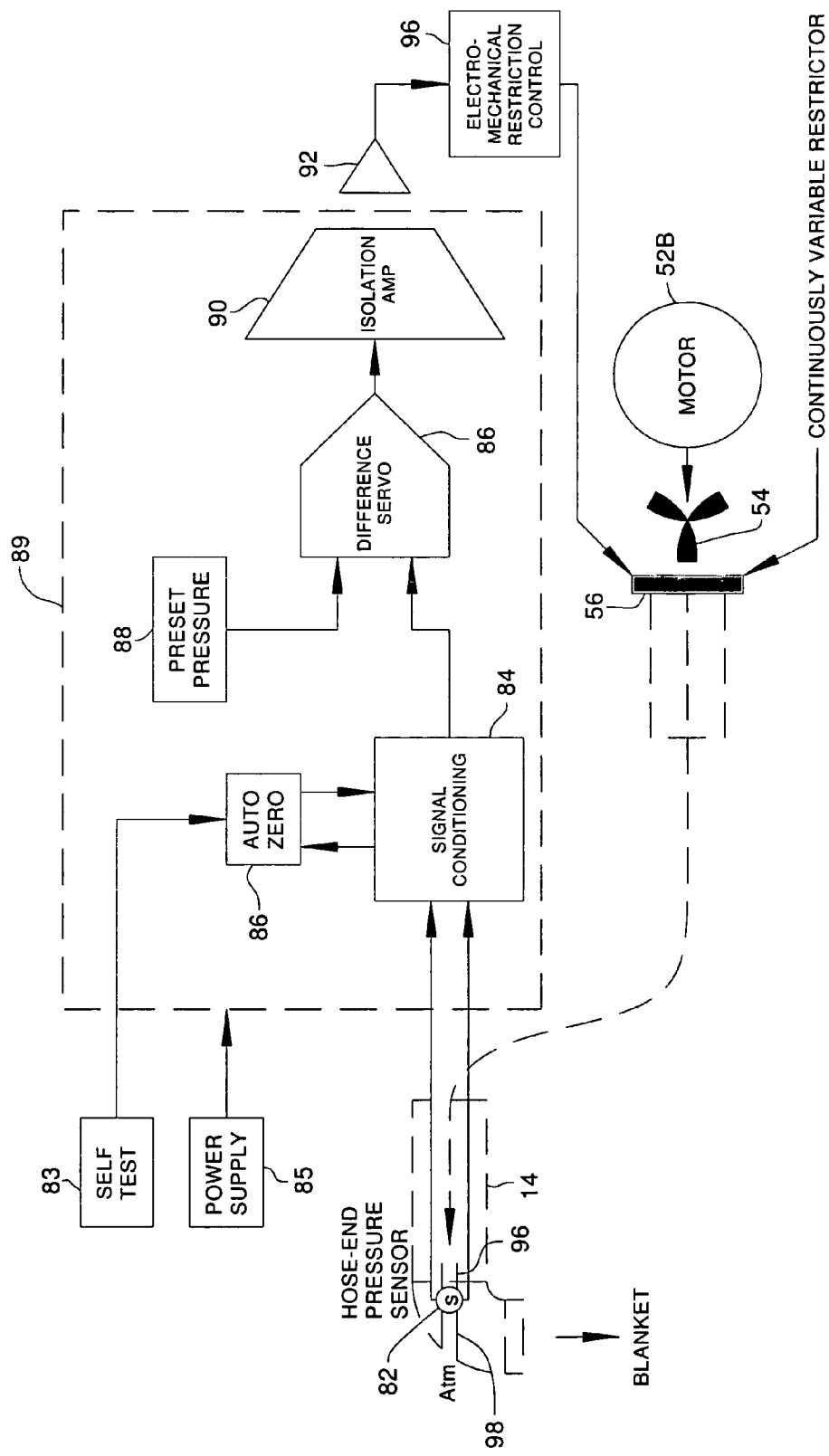
FIG. 15 is a schematic block diagram illustrating the remote sensor pressure servo circuit that can vary the speed of the air provided to a warming blanket connected to a convection warmer.

For the embodiments of FIG. 14 and the to be discussed FIG. 15, the sensor is placed with the semiconductor portion facing the airflow, so that there is a pressure differential between the front of the sensor that faces the airflow 96 and the back of the sensor referenced to the atmosphere 98. As a consequence, a differential signal is generated by the sensor, in response to the pressure of the air moving past the sensor.

This is sent to a signal conditioning circuit 84. Signal conditioning circuit 84 converts the low level differential signal from sensor 82 to a signal that is readable. In addition, signal conditioning circuit 84 filters out ambient noises from the input signal.

Connected to signal conditioning circuit 84 is an auto zero circuit 86, which when the system is turned on but before motor 52a is activated, provides a baseline by which the signal conditioning circuit 84 compares with the incoming differential signal from sensor 82. In effect, the auto zero circuit 86 is a sample and hold circuit that establishes a base number or signal for comparison purposes. A self test circuit 83 provides an input to the auto zero circuit 86 for zeroing the sensor offset when the system is first powered on. As shown, a power supply 85 provides the power for the various circuits of the feedback circuit 89, designated by the dotted line.

The sensed signal, which now has been compensated by the auto zero circuit, is forwarded to a difference servo circuit 86, which is conditioned to output the difference from the preset pressure 88 that is also connected as an input to difference servo circuit 86. The preset pressure circuit 88 has, as its name implies, a preset pressure that, once set, does not need to be reset. For the various warming blankets being addressed by the instant invention convection warmer, it has been found that a desirable preset pressure should be within a range of 0.005 to 0.02 psi, with 0.01 psi being a possible optimal or desirable pressure for the inflated blankets. This preset pressure is fed to the difference servo 86 at power up of the system. The difference between the preset pressure and the output of the signal conditioning unit 84 is output as a difference signal to an isolation amplifier 90, which is coupled to the receiving amplifier 92 for providing a signal to a motor speed controller 94, which in turn drives motor 52a at the appropriate speed.

In operation, upon sensing the pressure of the air, sensor 82 transmits the pressure, as a differential signal, to signal conditioning circuit 84, which offsets the signal with the baseline signal provided by auto zero circuit 86. The difference signal is then amplified and fed to difference servo circuit 86 via line 85, and is compared with the preset pressure, sent via line 87, by preset pressure circuit 88. If the sensed pressure is deemed to be lower than the preset pressure, then the difference servo circuit 86 will send out a signal to motor speed controller 94 to increase the speed of motor 52a so that fan 54 can move a large amount of air to hose 14. As the flow rate of air provided to the outlet increases so does the pressure, and as the difference between the preset pressure and the sensed pressure narrows, the speed of the motor 52a is decreased, so as to decrease the flow rate of the air being provided to the outlet.

Thus, a feedback circuit is established for maintaining the pressure sensed by sensor 82 positioned within hose 14 to substantially that of the preset pressure, to thereby maintain the pressure in the blanket to an optimal pressure between the range of 0.005 to 0.02 psi, irrespective of the dimension of the blanket that is connected to the outlet of the warmer via hose 14. Since each of the warming blankets has holes or slits where through heated air is leaked out to warm the patient covered by the blanket, by the feedback circuit of the FIG. 14 embodiment, the pressure within the blanket is maintained even though there may be different number of (as well as differently configured) holes or slits for the different blankets of different sizes.

FIG. 15 illustrates an embodiment that is similar to the embodiment of FIG. 14, but motor 52b being a fixed speed motor, and the flow rates are controlled by valve 56 by means of an electro-mechanical restriction controller 96. As noted before with respect to the various embodiments that utilize the variable valve 56, the pressure at the outlet, as exemplified by hose 14, detected by senor 82 is compared with a preset pressure for controlling the operation of the electro-mechanical restriction controller 96, which in turn controls the amount of air allowed by valve 56 to pass through to hose 14. With the embodiments of FIGS. 14 and 15, blankets of various dimensions may all be used with the convection warmer of the instant invention without altering the outlet hose, as the flow rate of air to be provided by the warmer is continuously monitored and varied, due to the feedback provided by feedback circuit 89.

Figure 16:
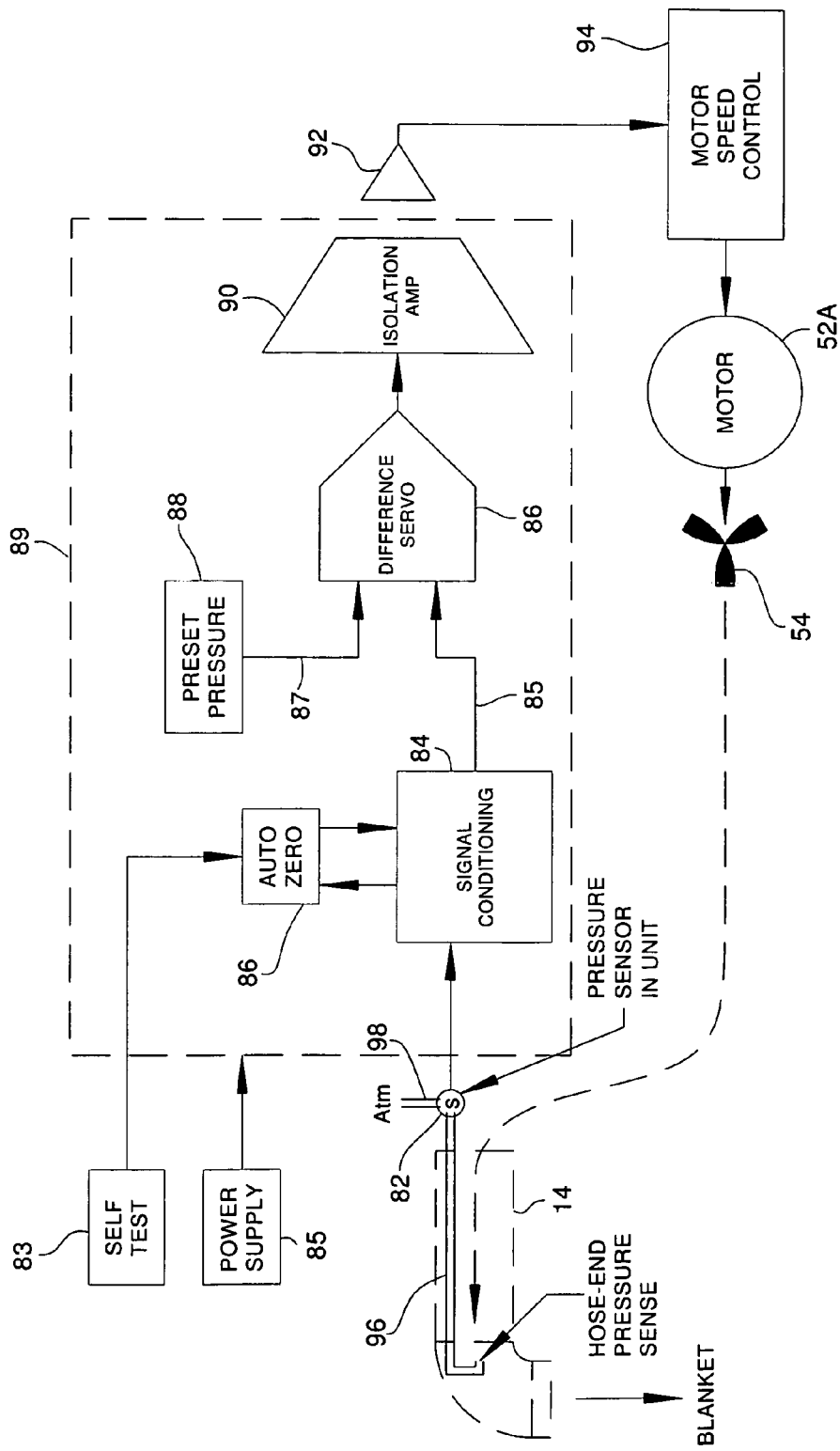
FIG. 16 is a remote sense servo circuit that can variably control the speed of a motor adapted to be used with a convection warmer.
Figure 17:
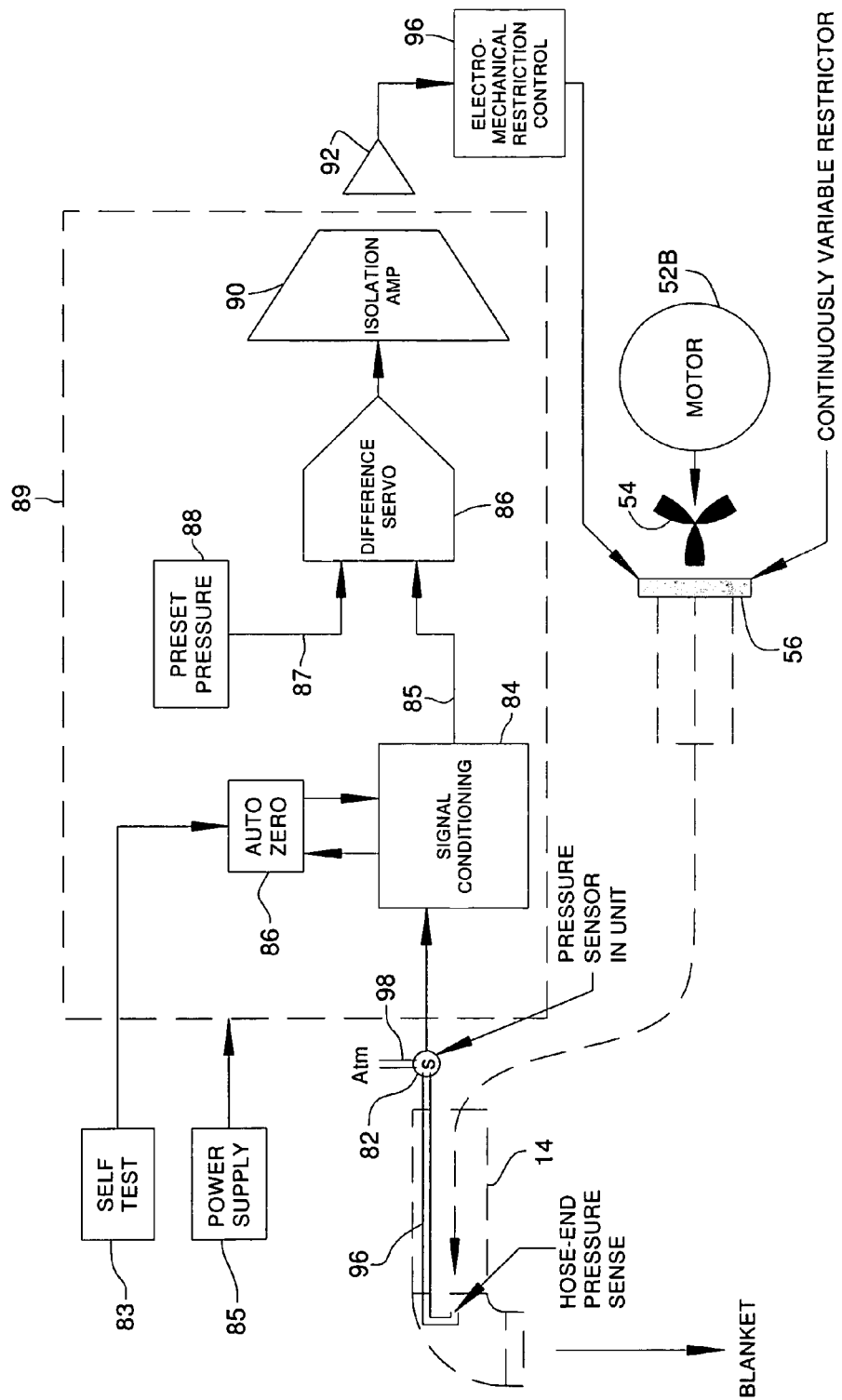
FIG. 17 is a schematic block diagram illustrating the remote sense pressure servo circuit that can vary the speed of the air provided to a warming blanket connected to a convection warmer.

The embodiments in FIGS. 16 and 17 are similar to the embodiments illustrated in FIGS. 14 and 15, respectively. As each of those embodiments encompasses a feedback circuit for varying the flow rate of air being provided to the outlet of the system, the sensed pressure is maintained substantially at the preset pressure. For the FIGS. 16 and 17 embodiments, the sensor 82, instead of being positioned within hose 14 or the outlet of the system, is positioned away from hose 14, for example within the cabinet enclosure of the warmer. Since sensor 82 is positioned away from the outlet and may therefore not be in direct contact with the air being provided to the outlet, to obtain a difference, sensor 82 detects the pressure within the outlet, or hose 14 via a conduit 96 that has an opening fitted to the end of hose 14. Sensor 82 further has a second conduit 98 that is open to atmosphere. Thus, sensor 82 is able to obtain a differential signal, between the sensed pressure inside hose 14 and atmospheric pressure. This differential signal is forwarded to the signal conditioning circuit 84 as was done in the embodiments disclosed in FIGS. 14 and 15. By thus locating sensor 82 away from hose 14, cost savings could be achieved, as sensor 82 is a relatively expensive item which, if positioned within hose 14, is disposed of along with hose 14, which oftentimes would need to be replaced due to it being damaged. On the other hand, by locating sensor 82 away from the disposable hose 14, provided that it stays operational, the same sensor could be used for an indefinite time.

The invention claimed is:

1. System for providing a fluid to a patient temperature regulating blanket comprising:
   a temperature regulating blanket;
   an outlet for establishing a fluid path to said patient temperature regulating blanket;
   a fluid mover for directing the fluid to said outlet;
   a controller for controlling the flow rate of the fluid to said outlet;
   at least one sensor located relative to said outlet adapted to sense the pressure of the fluid at said outlet; and
   a circuit for utilizing the sensed pressure of the fluid from said sensor to instruct said controller to, if needed, vary the flow rate of the fluid to said outlet for maintaining the sensed pressure substantially at a preset pressure so that the blanket is property inflated with the fluid to effect an optimal clinical temperature environment for a patient using the blanket;
   wherein said fluid is air and wherein said sensor is positioned away from said outlet but in fluid communication with the air in said outlet for sensing the pressure of the air at said outlet, said sensor further being in communication with atmospheric pressure, said sensor comparing the sensed pressure at said outlet with the sensed atmospheric pressure for outputting a difference signal to said circuit.

2. System of claim 1, wherein said fluid mover comprises a variable speed air blower, said controller controlling the speed of said blower to direct air to said outlet in response to the pressure sensed by said sensor and relayed to said circuit, said circuit using the sensed pressure from said sensor as a feedback to instruct said controller to control the speed of said blower to thereby ensure that the sensed pressure of the air directed by said blower to said outlet does not substantially deviate from the preset pressure.

3. System of claim 1, wherein said fluid mover comprises an air blower, and wherein said controller comprises a valve adapted to control the amount of air directed by said blower to said outlet, said circuit using the sensed pressure from said sensor as a feedback for said valve to control the amount of air provided to said outlet at a given period of time and therefore the flow rate of air provided to said outlet to ensure that the sensed pressure of the air directed by said blower to said outlet does not substantially deviate from the preset pressure.

4. System of claim 1, wherein said blanket is selected from among a plurality of blankets of different dimensions for use by patients of different sizes, each of the plurality of blankets having a corresponding inlet fittingly connectable to said outlet, wherein each of me plurality of blankets requires a given desired flow rate in order to be inflated by the fluid at the preset pressure.

5. System of claim 1, further comprises a heater for heating the fluid, the heated fluid being fed to the blanket for warming a patient covered by the blanket.

6. System of claim 1, wherein said preset pressure is approximately 0.005 to 0.05 psi.

7. System for providing a fluid to a patient warming blanket, comprising:
   an outlet for establishing a fluid path to the blanket;
   a fluid mover for directing the fluid to said outlet, said fluid mover adapted to move the fluid at variable flow rates;
   a controller for controlling said fluid mover to move the fluid to the blanket;
   at least one sensor located relative to said outlet adapted to sense the pressure of the fluid at said outlet; and
   a circuit for utilizing the sensed pressure of the fluid from said sensor to instruct said controller to control said fluid mover to continuously vary the flow rate of the fluid fed to said outlet so as to maintain the sensed pressure substantially at a preset pressure;
   wherein said fluid is air and wherein said sensor is positioned away from said outlet but in fluid communication with The air in said outlet for sensing the pressure of the air at said outlet, said sensor further being in communication with atmospheric pressure, said sensor comparing the sensed pressure at said outlet with the sensed atmospheric pressure for outputting a difference signal to said circuit.

8. System of claim 7, wherein said fluid mover comprises a variable speed air blower, said controller controlling the speed of said blower to direct air to said outlet in response to the pressure sensed by said sensor and relayed to said circuit, said circuit using the sensed pressure from said sensor as a feedback to instruct said controller to controllably vary the speed of said blower so that said blanket is maintained at substantially the preset pressure after being inflated.

9. System for providing a fluid to a patient warming blanket, comprising:
   an outlet for establishing a fluid path to the blanket;
   a fluid mover for directing the fluid to said outlet;
   a valve adapted to variably control the flow rate of the fluid to be moved to said outlet;
   a controller for controlling said valve to move the fluid to the blanket;
   at least one sensor located relative to said outlet adapted to sense the pressure of the fluid at said outlet; and
   a circuit for utilizing the sensed pressure of the fluid from said sensor to control said valve to, if needed, vary the flow rate of the fluid provided to said outlet so as to maintain the sensed pressure substantially at a preset pressure;
   wherein said fluid is air and wherein said sensor is positioned away from said outlet but in fluid communication with the air in said outlet for sensing the pressure of the air at said outlet, said sensor further being in communication with atmospheric pressure, said sensor comparing the sensed pressure at said outlet with the sensed atmospheric pressure for outputting a difference signal to said circuit.

10. A method of providing a fluid to a patient warming blanket fluid, comprising the steps of:
   a) providing an outlet for establishing a fluid path to the blanket;
   b) utilizing a fluid mover for directing the fluid to said outlet;
   c) controlling the flow rate of the fluid directed to said outlet;
   d) locating at least one sensor relative to said outlet for sensing the pressure of the fluid at said outlet; and
   e) utilizing the sensed pressure of the fluid from said sensor to continuously control the flow rate of the fluid provided to said outlet so as to maintain the sensed pressure substantially at a preset pressure;
   wherein said fluid is air and wherein step d comprises the step of:
   positioning said sensor away from said outlet but in fluid communication with the air in said outlet for sensing the pressure of the air at said outlet, said sensor further being in communication with atmospheric pressure; and
   wherein step e further comprises the step of:
   comparing the sensed pressure at said outlet with the sensed atmospheric pressure for outputting a difference signal.

11. Method of claim 10, wherein said said fluid mover comprises a variable speed air blower, wherein step e further comprises the steps of:
   controlling the speed of said blower to direct air to said outlet in response to the pressure sensed by said sensor; and
   using the sensed pressure from said sensor as a feedback to vary the speed of said blower to ensure that the pressure of the air directed by said blower to said outlet does not substantially deviate from the preset pressure.

12. Method of claim 10, wherein said fluid mover comprises an air blower, wherein step c further comprises the step of:
   utilizing a valve to control the amount of air directed by said blower to said outlet; and
   wherein said step e further comprises the steps of:
   using the sensed pressure from said sensor as a feedback for said valve to control the amount of air provided to said outlet at a given period of time; and
   controlling said valve to provide air to the blanket at an optimal flow rate so that the pressure of the air inflating the blanket does not substantially deviate from the preset pressure.

* * * * *